United States Patent [19]

Kaiser et al.

[11] Patent Number: 4,857,540

[45] Date of Patent: Aug. 15, 1989

[54] DOPAMINE-β-HYDROXYLASE INHIBITORS

[75] Inventors: Carl Kaiser, Haddon Heights; Lawrence I. Kruse, Haddonfield, both of N.J.

[73] Assignee: SmithKline Beckman Corporation, Philadelphia, Pa.

[21] Appl. No.: 126,084

[22] Filed: Nov. 27, 1987

Related U.S. Application Data

[62] Division of Ser. No. 689,680, Jan. 8, 1985, Pat. No. 4,728,741.

[51] Int. Cl.$^4$ ............................................. A61K 31/415
[52] U.S. Cl. .................................... 514/387; 514/394; 514/395; 548/305; 548/329; 548/330
[58] Field of Search ....................... 548/305, 329, 330; 514/387, 394, 395

[56] References Cited

FOREIGN PATENT DOCUMENTS 424258 2/1942 Japan ................................. 514/395

OTHER PUBLICATIONS

Tyurenkova et al., *Khim Geterotsikl. Soedin*, 1980, No. 6, pp. 818–821.
Bianchi et al., *Eur. J. Med. Chem.*, 1981, vol. 16, No. 4, pp. 321–326.
Chemical Abstracts, vol. 58, No. 12, Abstract No. 139644, Jun. 10, 1963 (Nakajima et al.).
Chemical Abstracts, vol. 69, No. 22, Abstract No. 96573r, Nov. 25, 1968 (Aryuzina et al.).

*Primary Examiner*—Mary C. Lee
*Assistant Examiner*—Zinna Northington
*Attorney, Agent, or Firm*—Stuart R. Suter; Alan D. Lourie

[57] ABSTRACT

1-substituted-2-mercapto(or aminomethyl)benzimidazole compounds which inhibit dopamine-β-hydroxylase activity.

44 Claims, No Drawings

DOPAMINE-β-HYDROXYLASE INHIBITORS

This is a division of application Ser. No. 689,680 filed Jan. 8, 1985 now U.S. Pat. No. 4,728,741.

This invention relates to inhibitors of dopamine-β-hydroxylase.

In the catecholamine biosynthetic pathway, tyrosine is converted in three steps to norepinephrine (NE). Intermediates are dihydroxyphenylalanine (DOPA) and dopamine (DA). The latter is hydroxylated to norepinephrine by dopamine-β-hydroxylase (DBH) in the presence of oxygen and ascorbic acid.

Inhibition of catecholamine activity has been found to decrease hypertension. See, for example Matta et al., *Clin. Pharmacol. Ther.* 14, 541 (1973), and Teresawa et al., *Japan Circ. J.* 35, 339 (1971). Weinshilboum, *Mayo Clin. Proc.* 55, 39 (1980), reviews compounds which inhibit catecholamine activity by interfering with adrenergic receptors. Alternatively, the catecholamine biosynthetic pathway can be suppressed at any of the three steps, resulting in decreased levels of NE. In addition to decreasing hypertension, inhibitors of NE synthesis are active as diuretics, natriuretics, cardiotonics and vasodilators. Inhibition of DBH activity can have the added advantage of increasing levels of DA, which as reported by Ehrreich and Korduba, "New Antihypertensive Drugs," Spectrum Publishing, 1976, pp. 409–432, has been found to have selective vasodilator activity at certain concentrations.

DBH inhibitors have also been shown to reduce or prevent formation of gastric ulcers in rats by Hidaka et al., "Caetcholamine and Stress," edit. by Usdin et al., Permagon Press, Oxford, 1976, pp. 159–165 and by Osumi et al., *Japan J. Pharmacol.* 23, 904 (1973).

A number of DBH inhibitors are known. These are generally divided into two classes, namely, metal chelating agents, which bind to copper in the enzyme, and phenethylamine analogues. Rosenberg et al., "Essays in Neurochemistry and Neuropharmacology, Vol. 4," edit. by Youdim et al., John Wiley & Sons 1980, p. 172–192, and Goldstein, *Pharmacol. Rev.* 18 (1), 77 (1966), review DBH inhibitors.

Known inhibitors include, among others: picolinic acids, [See, Claxton et al., *Eur. J. Pharmacol.* 37, 179 (1976) and Runti et al., *Il. Farmaco Sci. Ed.* 36, 260 (1980)]; 2-(2-benzimidazolyl)amino-2-imidazoline dihydrochloride [See, Claxton, cited above]; and 1-alkyl-2-mercaptoimidazoles [See, Thorogood, European Patent Application No. 951 and Fuller et al., *Adv. Enzyme Regul.* 15, 267 (1976)].

DBH hydroxylates a variety of phenethylamine substrates. Rosenberg et al., "Essays in Neurochemistry and Neuropharmacology," Vol. 4, edit. by Youdim et al. John Wiley & Sons, 1980, pp. 163–209, extensively review the chemistry of DBH, including, at pp. 176–179 and 196–202, proposed mechanisms of action. There is not yet a known satisfactory model of the mechanism of action of DBH.

Although there are many known inhibitors of DBH, none of these agents has found clinical application because of non-specific, often toxic, properties they possess. Fusaric acid, for example, has been found to be hepatotoxic. See, for example, Teresawa et al., *Japan, Cir. J.* 35, 339 (1971) and references cited therein.

Co-pending European Patent Application No. 84302 442.5-2101 (Publication No. 125783) discloses a series of imidazole derivatives having a phenylalkylene substituent in the 1-position and a carboxylic acid or aminomethyl moiety in the 2-position which have been found to inhibit DBH activity. In addition, co-pending European Patent Application No. 84302423.3-2101 (Publication No. 125033) discloses a related series of 1-phenylalkylene imidazoles having a mercapto moiety in the 2-position.

Further, Lin et al., *Canad. J. Chem.* 52 (13), 2359–2366 (1974) report preparation of 1-phenyl-2-mercaptobenzimidazole, that is the compound of formula

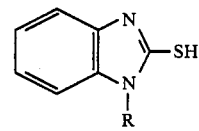

in which R is $C_6H_5-$, but does not disclose a pharmaceutical use for the compound; and Terent'ev et al., *Zh. Obshch. Khim.*, 40, 1605-7, 1970, discloses 1-benzyl-, and 1-phenylethyl-2-mercaptobenzimidazole, that is a compound of the above structure in which R is $PhCH_2$ and $Ph(CH_2)_2$, but does not disclose a pharmaceutical use for the compounds.

In addition, GB No. 1,217,138 discloses a pharmaceutical composition having anti-inflammatory activity comprising 1-(4-methoxyphenyl)-2-mercaptobenzimidazole, that is the compound of the above structure in which R is $-C_6H_4-4-OCH_3$; and El-Sabaii et al., *J. Pharm. Sci.* 69 (11), 1348–50, (1980), discusses the evaluation of 2-mercaptobenzimidazoles as anti-cancer agents.

The present invention relates to substituted benzimidazole derivatives which have been found to inhibit dopamine-β-hydroxylase activity in mammals.

In one aspect of the invention, there is therefore provided novel compounds of structure (I)

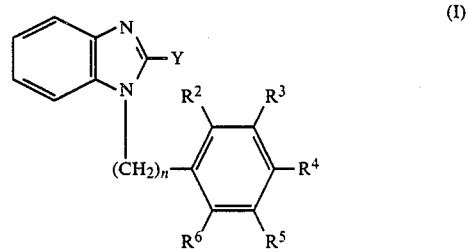

(I)

in which:
Y is $-CH_2NH_2$ or SR;
R is hydrogen or $C_{1-4}$ alkyl;
n is 0 to 5; and
$R^2$ to $R^6$ are the same or different and are each hydrogen, halogen, hydroxy, $C_{1-4}$ alkyl, CN, $NO_2$, $SO_2NH_2$, $CO_2H$, $CONH_2$, CHO, $CH_2OH$, $CF_3$, $C_{1-4}$alkoxy, $SO_2C_{1-4}$alkoxy, $SO_2C_{1-4}$-fluoroalkyl or $CO_2C_{1-4}$alkyl, provided that,
(i) when Y is SH, $R^2$, $R^3$, $R^5$ and $R^6$ are all hydrogen and n is 0, $R^4$ is not methoxy; and
(ii) when Y is SH, $R^2$, $R^3$, $R^5$ and $R^6$ are all hydrogen and n is 0, 1 or 2, $R^4$ is not hydrogen;
or a pharmaceutically acceptable salt or hydrate thereof.

Within the scope of structure (I), there is provided compounds of structure (IA)

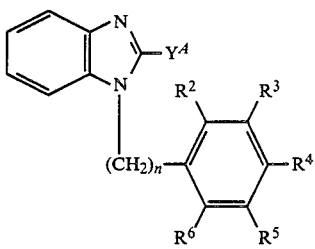

in which:
Y$^A$ is SR; and n, R and R$^2$ to R$^6$ are as described for structure (I); provided that
(i) when R is H, R$^2$, R$^3$, R$^5$ and R$^6$ are all hydrogen and n is 0, R$^4$ is not methoxy;
(ii) when R is H, R$^2$, R$^3$, R$^5$ and R$^6$ are all hydrogen and n is 0, 1 or 2, R$^4$ is not hydrogen;
or pharmaceutically acceptable salt or hydrate thereof.

Suitably R is C$_{1-4}$ alkyl, for example, methyl. Preferably R is hydrogen.

Preferably n is 1 to 3.

Suitably, R$^2$, R$^3$, R$^5$ and R$^6$ are all hydrogen and R$^4$ is hydroxy or C$_{1-4}$ alkoxy, for example methoxy. Preferably, two of R$^2$, R$^3$, R$^5$ and R$^6$ are halogen, for example chloro or fluoro, the other two are hydrogen and R$^4$ is hydrogen, hydroxy or C$_{1-4}$ alkoxy, for example methoxy.

In particular, preferred compounds of structure (IA) are those in which Y is SH, n is 1, R$^3$ and R$^5$ are both chlorine or fluorine and R$^4$ is hydrogen, hydroxy, or methoxy for example:
1-(3,5-dichloro-4-methoxybenzyl)-2-mercaptobenzimidazole
1-(3,5-difluoro-4-methoxybenzyl)-2-mercaptobenzimidazole
1-(3,5-dichlorobenzyl)-2-mercaptobenzimidazole
1-(3,5-difluorobenzyl)-2-mercaptobenzimidazole
1-(3,5-dichloro-4-hydroxybenzyl)-2-mercaptobenzimidazole
1-(3,5-difluoro-4-hydroxybenzyl)-2-mercaptobenzimidazole.

Within the scope of compounds of structure (I), but outside the scope of structure (IA) there is also provided compounds of structure (IB)

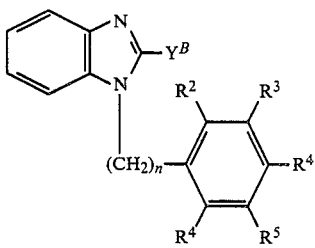

in which :
Y$^B$ is —CH$_2$NH$_2$; and
n and R$^2$ to R$^6$ are as defined in structure (I),
or a pharmaceutically acceptable salt or hydrate thereof.

Preferably n is 1 to 3.

Suitably, R$^2$ to R$^6$ are all hydrogen. Preferably one or two of R$^2$ to R$^6$ are halogen, and the others are hydrogen.

In particular, preferred compounds of structure (IB) are those in which n is 1 and R$^3$ and R$^4$ are both chlorine, for example:
1-[3,4-dichlorobenzyl]-2-aminomethylbenzimidazole dihydrochloride.

In a further aspect of the invention there is provided pharmaceutical compositions comprising a compound of structure (II)

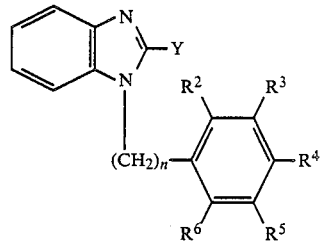

in which:
Y is CH$_2$NH$_2$ or SR;
R is hydrogen or C$_{1-4}$ alkyl;
n is 0 to 5; and
R$^2$ to R$^6$ are the same or different and are each hydrogen, halogen, hydroxy, C$_{1-4}$ alkyl, CN, NO$_2$, SO$_2$NH$_2$, CO$_2$H, CONH$_2$, CHO, CH$_2$OH, CF$_3$, C$_{1-4}$alkoxy, SO$_2$C$_{1-4}$alkoxy, SO$_2$C$_{1-4}$-fluoroalkyl or CO$_2$C$_{1-4}$alkyl, provided that when Y is SH, R$^2$, R$^3$, R$^5$ and R$^6$ are all hydrogen and n is 0, R$^4$ is not methoxy;
or a pharmaceutically acceptable salt or hydrate thereof in association with a pharmaceutically acceptable carrier.

In a yet further aspect of the present invention there is provided a method of inhibiting dopamine-$\beta$-hydroxylase activity in mammals which comprises administering internally to a subject in need thereof, an effective amount of a compound of structure (III)

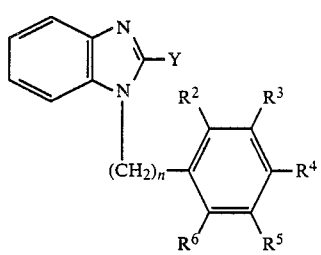

in which
Y is a group —CH$_2$NH$_2$ or SR;
R is hydrogen or C$_{1-4}$alkyl;
n is 0 to 5;
R$^2$ to R$^6$ are the same or different and are each hydrogen, halogen, hydroxy, C$_{1-4}$ alkyl, CN, NO$_2$, SO$_2$NH$_2$, CO$_2$H, CONH$_2$, CHO, CH$_2$OH, CF$_3$, C$_{1-4}$alkoxy, SO$_2$C$_{1-4}$alkoxy, SO$_2$C$_{1-4}$ fluoroalkyl or CO$_2$C$_{1-4}$alkyl;
or a pharmaceuticaly acceptable salt or hydrate thereof.

In a still further aspect of the present invention there is provided a process for the preparation of compounds of structure (I) which comprises:
(a) where Y is SH, cyclization of a compound of structure IV(a)

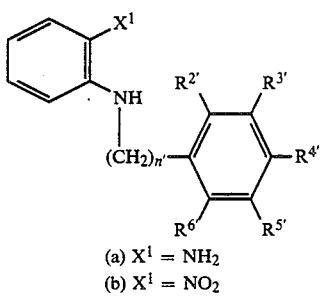

(a) $X^1 = NH_2$
(b) $X^1 = NO_2$ in which, n' is 0 to 5 and $R^{2'}$ to $R^{6'}$ are selected from hydrogen, halogen, $C_{1-4}$ alkyl, CN, $NO_2$ $SO_2NH_2$, $CO_2H$, $CONH_2$, CHO, $CH_2OH$, $CF_3$, $C_{1-4}$alkoxy, $SO_2C_{1-4}$fluoroalkyl or $CO_2C_{1-4}$alkyl;

(b) where Y is SR and R is $C_{1-4}$ alkyl, alkylation of a compound of structure (I) in which Y is SH; and (c) where Y is $CH_2NH_2$, reduction of a compound of structure XII(b)

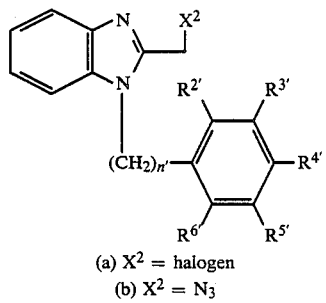

(a) $X^2$ = halogen
(b) $X^2 = N_3$ in which, n' and $R^{2'}$ to $R^{6'}$ are as described in structure (IV); and, optionally, converting the compound of structure (I) so formed into a pharmaceutically acceptable salt or hydrate.

In yet a further aspect of the present invention there are provided novel intermediates of structures IV(a) and (b), and XII(a) and (b) which are useful in the preparation of compounds of structure (I):

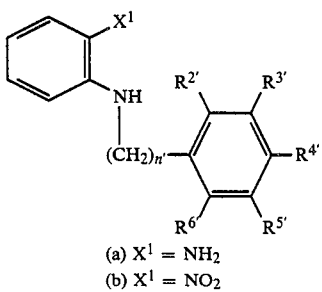

(a) $X^1 = NH_2$
(b) $X^1 = NO_2$ in which, n' is 0 to 5 and $R^{2'}$ to $R^{6'}$ are selected from hydrogen, halogen, $C_{1-4}$ alkyl, CN, $NO_2$ $SO_2NH_2$, $CO_2H$, $CONH_2$, CHO, $CH_2OH$, $CF_3$, $C_{1-4}$alkoxy, $SO_2C_{1-4}$fluoroalkyl or $CO_2C_{1-4}$alkyl;

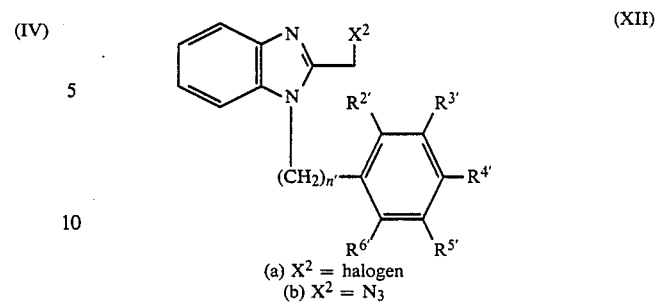

(a) $X^2$ = halogen
(b) $X^2 = N_3$ in which n' and $R^{2'}$ to $R^{6'}$ are described for structure (IV).

It is to be understood that the foregoing structures include the thione tautomers of compounds in which Y is SH ie. compounds in which Y is =S.

Further it will be appreciated and understood by persons skilled in the art that due to free-rotation around the bond between the phenyl group and alkylene group (or where n=0, the benzimidazole ring) substituents $R^2$ and $R^6$ and $R^3$ and $R^5$ are effectively equivalent.

The novel compounds of the present invention and compounds used in the compositions and methods of the invention can be prepared by methods analogous to those known in the art.

For example, compounds of structure (I) in which Y is SH can be prepared by cyclization of a compound of structure IV(a)

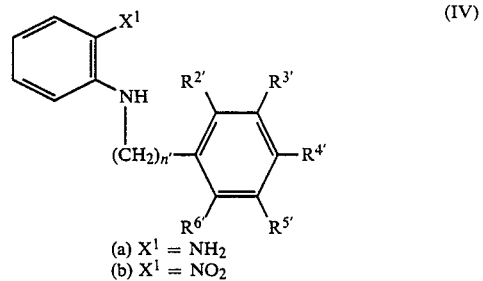

(a) $X^1 = NH_2$
(b) $X^1 = NO_2$ in which:
n' is 0 to 5; and
$R^{2'}$ and $R^{6'}$ are selected from hydrogen, halogen, $C_{1-4}$ alkyl, CN, $NO_2$ $SO_2NH_2$, $CO_2H$, $CONH_2$, CHO, $CH_2OH$, $CF_3$, $C_{1-4}$ alkoxy, $SO_2C_{1-4}$ fluoroalkyl or $CO_2C_{1-4}$ alkyl.

It is to be noted, and will be apparent to persons skilled in the art that the combination of substituents $R^{2'}$ to $R^{6'}$ (and of $R^2$ to $R^6$ in formula (IA), (IB), (II) and (III)) is limited to those combinations which are accessible and which do not result in significant instability due to steric hindrance.

The cyclization of intermediates IV(a) to the desired compounds of structure (I) is carried out under basic conditions in the presence of carbon disulfide. Suitable basic conditions will be apparent to those skilled in the art, for example, aqueous sodium hydroxide in ethanol.

The intermediates of structure IV(a) can be prepared by reduction of the corresponding nitro-amino derivatives of structure IV(b). The reaction can be carried out using chemical reducing agents such as $SnCl_2$, $TiCl_3$ or $Fe/CH_3CO_2H$, or catalytic hydrogenation over a noble metal catalyst, for example, palladium or platinum.

Preferably, the reduction is carried out by way of catalytic hydrogenation over Raney nickel.

The nitro-amino intermediates of structure IV(b) can be prepared by reaction of an appropriate activated nitrobenzene of structure (V)

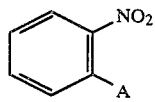

in which A is a suitable displaceable group, with a phenyl alkylamine of structure (VI)

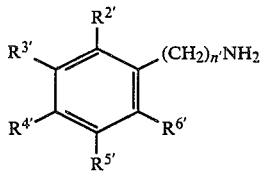

in which n', and $R^{2'}$ to $R^{6'}$ are as described for structure (IV).

Displaceable groups A will be apparent to these skilled in the art, for example, suitably A is bromo, iodo or nitro, preferably A is fluoro or chloro.

Compounds of structure (VI) are available in the art or can be prepared by methods analogous to those known in the art.

For example, compounds of structure (VI) in which n' is 1 to 5 can be prepared from readily available precursors (VII), (IX) or (X) as shown in Scheme 1:

Scheme 1

Procedure A

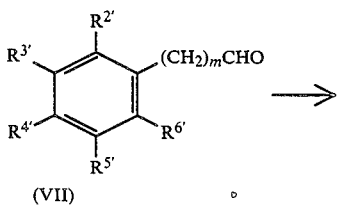

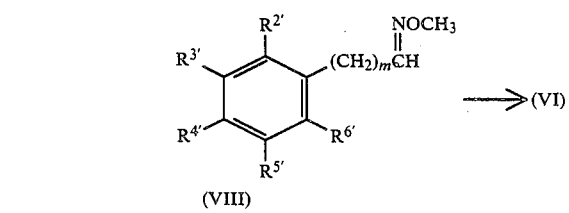

Procedure B

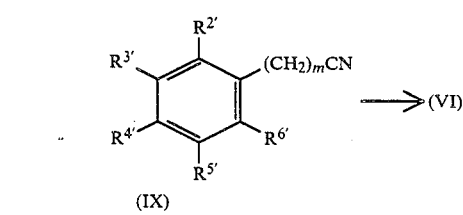

Procedure C

-continued
Scheme 1

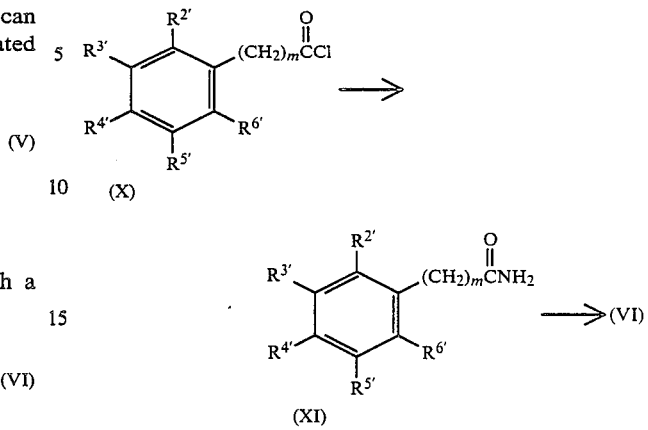

In structures (VII), (VIII), (IX), (X) and (XI), m is 0 to 4, and $R^{2'}$ to $R^{6'}$ are as described for structure (IV).

In procedure A, the starting aldehyde (VII) is reacted with a suitable oxime (methoxime is illustrated as an example) in the presence of for example ethanol/pyridine. Intermediate (VIII) so formed is then reduced to the desired phenylalkylamine (VI). Suitable reducing agents will be apparent to those skilled in the art and will depend on the nature of the substitution pattern $R^{2'}$ to $R^{6'}$ in (VIII), and include, for example, hydrogenation over palladium, platinum oxide or Raney nickel, or chemical reducing agents such as $AlH_3$, $LiAlH_4$ or $BH_3$.

Alternatively, compounds of structure (VI) in which n is 1 to 4 can be prepared by reduction of the corresponding benzonitrile (IX) (procedure B). Suitable reaction conditions will be apparent to those skilled in the art and include, for example hydrogenation over Raney nickel in the presence of ammonia.

In addition, compounds of structure (VI) in which n is 1 to 4 can be prepared by reaction of an appropriate phenylalkanoic acid chloride (X) with ammonia followed by reduction of the intermediate amide (XI) so formed (procedure C). Suitable reducing agents will be apparent to these skilled in the art and include for example, borane in tetrahydrofuran.

Compounds of structure (VI) in which n is 0, are substituted aniline derivatives which are known in the art or can readily be prepared by procedures well known to those skilled in the art.

Compounds of structure (I) in which Y is $-SC_{1-4}$ alkyl can be prepared from the corresponding compounds of structure (I) in which Y is SH, by, for example, alkylation in the presence of an alkylating agent in an inert solvent. Suitable alkylating agents include alkyl halides or tosylates and suitable inert solvents include, methanol, tetrahydrofuran and aqueous dimethylformamide. Preferred alkylating agents are alkyl iodides, for example, methyl iodide.

Compounds of structure (I) in which Y is $CH_2NH_2$ can also be prepared from the diamino compounds of structure IV(a) as follows:

Cyclization of a compound of structure IV(a) in the presence of an appropriate haloacetic acid under acid conditions according to the procedure of Jerchel et al., *Ann.* 575, 162, 1952, affords 2-halomethylbenzimidazoles of structure XII(a) either as free bases or as the acid addition salts:

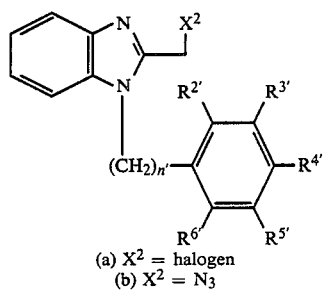

(a) $X^2$ = halogen
(b) $X^2$ = $N_3$ in which n', and $R^{2'}$ to $R^{6'}$ are as described for structure (IV).

Treatment of the 2-halomethylbenzimidazoles XII(a) with an alkali metal azide in a suitable solvent, affords 2-azidomethylbenzimidazoles of structure XII(b). Suitable alkali metal azides include lithium, sodium or potassium azide; suitable solvents include, aqueous N,N-dimethylformamide, N-methylpyrrolidinone, N,N-dimethylacetamide, hexamethylphosphoric triamide or alcohols. Preferably, sodium azide in aqueous DMF is used.

The desired compounds (I) are then prepared by reduction of the 2-azidomethyl intermediates XII(b) using a suitable reducing agent. The nature of the reducing agent will depend on the substitution pattern $R^{2'}$ to $R^{6'}$, and includes chemical reducing agents such as hydrogen sulfide: triphenylphosphorane/ammonia; $TiCl_3$; $FeSO_4$; $Zn/CH_3CO_2H$ or sodium borohydride; and hydrogenation over a noble metal catalyst such as platinum, palladium or Raney nickel. Preferably, the reduction is achieved by hydrogenation in presence of Raney nickel.

Where it is desired in the final product for a hydroxyl group to be present in one or more of $R^2$ to $R^6$, the corresponding O-alkyl compound is prepared and the alkyl group then removed to give the free OH group. Preferably, the foregoing reactions are carried out on the O-methyl ethers which are deprotected using any one of the number of reagents known in the art, for example, $AlCl_3$, $BBr_3$, HBr in water or acetic acid, hydrogen iodide or methanesulfonic acid with or without methionine.

The pharmaceutically acceptable acid addition salts of the compounds wherein Y is SR and R is $C_{1-4}$ alkyl, and Y is $CH_2NH_2$ are formed with strong or moderately strong organic or inorganic acids by methods known to the art. For example, the base is reacted with an inorganic or organic acid in an aqueous miscible solvent such as ethanol with isolation of the salt by removing the solvent or an an aqueous immiscible solvent when the acid is soluble therein, such as ethyl ether or chloroform, with the desired salt separating directly or being isolated by removing the solvent. Exemplary of the salts which are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts.

The compounds of the invention and the compounds used in the method and pharmaceutical composition of the invention, because they can be used to inhibit DBH activity, have therapeutic value as diuretic, natriuretic, cardiotonic, antihypertensive and vasodilator agents, as well as antiulcerogenic and anti-Parkinsonism agents. An advantageous feature of the compounds is their high degree of lipophilicity. This feature increases in vivo potency by facilitating transport into adrenergic neurons.

Compounds of the invention and other compounds useful in the method of the invention were screened for in vitro DBH inhibition by a standard procedure for assaying conversion of tyramine to octopamine in the presence of DBH. Octopamine was assayed following sodium periodate oxidation to p-hydroxybenzaldehyde by measuring spectrophotometric absorbance at 330 nm. Results are given in Table I, below. Inhibition is given in molar concentration of compound at which DBH activity was halved ($IC_{50}$). Melting points (mp) are given in °C. By this procedure fusaric acid was found to have an $IC_{50}$ of about $8 \times 10^{-7}$.

TABLE I

| Example No. | $IC_{50}$ value | M.P. °C. |
|---|---|---|
| 2 | 60% at $10^{-4}$ M | 234–235[1] |
| 4 | 70% at $10^{-4}$ M | 233[1] |
| 5 | $6.1 \times 10^{-5}$ | 185[1] |
| 6 | $6.2 \times 10^{-6}$ | 179–180[1] |
| 7 | 6% at $10^{-4}$ M | 199–200[1] |
| 8 | $3.8 \times 10^{-6}$ | 240–243[2] |
| 9 | $6.6 \times 10^{-7}$ | 200[3] |
| 10 | $1.3 \times 10^{-5}$ | 216–200[2] |
| 37 | $1.2 \times 10^{-7}$ | 260–262 (dec) |
| 38 | $6.9 \times 10^{-5}$ | 193–196 (dec) |
| 39 | $1.3 \times 10^{-4}$ | 190–193° |
| 40 | $1.13 \times 10^{-4}$ | 169–172° |

[1] recrystallized from ethanol
[2] ethyl acetate/hexane
[3] ethyl acetate/hexane/petroleum ether Various compounds of the invention were tested for their effects in vivo on peripheral dopamine (DA) and norepinephrine (NE) levels substantially by the procedure of DaPrada and Zürcher, Life Sci., 19, 1161, (1976). Spontaneously hypertensive rats were dosed twice, the second dose being about 18 hours after the first, and were sacrificed about 2 hours after the second dose. Averaged results, expressed in micrograms of DA and NE per gram of tissue are given in Table II.

TABLE II

| Compound | No. of Animals | DA µg/g | NE µg/g | DA/NE Ratio |
|---|---|---|---|---|
| Control ($H_2O$) | 5 | $0.297 \pm 0.02$ | $6.99 \pm 0.51$ | $0.042 \pm 0.002$ |
| Example 3 | 5 | $0.397 \pm 0.058$ | $7.82 \pm 0.73$ | $0.055 \pm 0.014$ |
| Example 6 | 5 | $0.607 \pm 0.03$ | $7.054 \pm 0.317$ | $0.086 \pm 0.0019$ |

Further, the same rats were dosed with a suspension or solution at a dose of 50 mg/kg of test compound i.p. and mean arterial blood pressure determined with indwelling cannulae inserted into the tail artery. A significant reduction in mean arterial pressure was recorded in rats dosed with 50 mg/kg i.p. of the compound of example 6.

The compounds can be incorporated into convenient dosage unit forms such as capsules, tablets or injectable preparations. Pharmaceutical carriers which can be employed can be solid or liquid. Solid carriers include, among others, lactose, terra alba, sucrose, talc, gelatin, agar, pectin, acacia, magnesium stearate, and stearic acid. Liquid carriers include, among others, syrup, peanut oil, olive oil and water. Similarly, the carrier or diluent may include any time delay material, such as glyceryl monostearate or glyceryl distearate, along or with a wax. The amount of solid carrier will vary widely but, preferably, will be from about 25 mg to about 1 g per dosage unit. If a liquid carrier is used, the preparation will be in the form of a syrup, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating and compressing, when necessary, for tablet forms, or mixing, filling and dissolving the ingredients, as appropriate, to give the desired oral or parenteral end products.

Doses of the present compounds in a pharmaceutical dosage unit will be an effective amount, that is, a nontoxic quantity selected from the range of 0.1–1000 mg/kg of active compound, preferably 10–100 mg/kg. The selected dose is administered to a patient in need of treatment from 1–5 times daily, orally, rectally, by injection or by infusion. Parenteral administration, which uses a low dose, is preferred. However, oral administration, at a higher dose, can also be used when safe and convenient for the patient.

The following examples are illustrative of preparation of compounds of the invention or intermediates thereof. The starting compounds of Examples 1, 4E, 4F, 8 and 9 are commercially available or are prepared by known techniques. The Examples are not intended to limit the scope of the invention as defined hereinabout and as claimed below. The compounds listed in Tables I and II, above, were prepared substantially by the illustrated procedures. All temperatures and melting points (mp) are in degrees Celsius (°C).

EXAMPLE 1

Preparation of 1-(3,5-dichlorobenzyl-4-methoxy)-2-mercaptobenzimidazole

A 3,5-Dichloro-4-methoxybenzaldehyde methoxime

A solution of 3,5-dichloro-4-methoxybenzaldehyde (10 g, 49 mmole) and methoxamine hydrochloride (4.6 g, 54 mmole) in 60 ml of 1:1 ethanol:pyridine was stirred at room temperature overnight. The mixture was evaporated, poured into water and extracted with dichloromethane. The organic layer was washed with 3N HCl (3×), once with water and once with aqueous sodium bicarbonate, then dried, ($Na_2SO_4$) and concentrated to give 10.8 g (94%) of the title compared, mp 80°.

B 3,5-Dichloro-4-methoxybenzylamine

A solution of 3,5-dichloro-4-methoxybenzaldehyde methoxime (10.7 g, 46 mmol) in freshly distilled tetrahydrofuran (THF) (60 ml) was cooled to 0° and stirred while 47 ml of 0.98M borane in THF was added. The resulting mixture was heated under reflux for 2 hours, cooled, and water (20 ml) added followed by 20% aqueous sodium hydroxide (20 ml). The mixture was heated under reflux for 2 hours, cooled and extracted twice with diethyl ether. The organic layer was extracted with 3N HCl, the aqueous layer made basic with 50% aqueous sodium hydroxide and the product was extracted into diethyl ether. The organic extracts were dried ($Na_2SO_4$) and concentrated to give 6.11 g (65%) of the title compound as a pale yellow oil.

C

N-(3,5-Dichloro-4-methoxybenzyl)-2-nitroaniline

A mixture of 3,5-dichloro-4-methoxybenzylamine (6 g, 29.2 mmole), 2-fluoronitrobenzene (2 g, 14.2 mmole) and ammonium acetate (1.0 g) was heated at 80° for 1 hour. The cooled mixture was taken up into ethyl acetate and washed sequentially with aqueous 3N HCl, water, aqueous 5% sodium bicarbonate, brine, dried ($Na_2SO_4$), and concentrated to give the title compound 4.0 g (78%) as orange crystals, mp 128°.

D

N-(3,5-Dichloro-4-methoxybenzyl)-2-aminoaniline, and 1-(3,5-Dichloro-4-methoxybenzyl)-2-mercaptobenzimidazole A solution of nitroaniline from C above (8.7 g, 26.7 mmole) in a mixture of methanol (280 ml) and N,N-dimethyl-formamide (20 ml) was heated at reflux and stirred mechanically while concentrated aqueous ammonium hydroxide (54 ml) and a solution of $FeSO_4.7H_2O$ (48.2 g) in water (54 ml) were added sequentially. The resulting black mixture was stirred vigorously and heated at reflux for 2 hours, then filtered. The filtrate was concentrated and the residue was dissolved in ethyl acetate which was washed three times with water and once with brine. The organic layer was dried ($Na_2SO_4$), and concentrated to give a solid which contained N-(3,5-dichloro-4-methoxybenzyl)-2-aminoaniline.

The residue was dissolved in ethanol (145 ml) and a solution of potassium hydroxide (2.5 g) in $H_2O$ (54 ml) and carbon disulfide (6.5 ml) was added. The solution was heated at reflux for 18 hours. The solution was cooled, poured into $H_2O$, acidified with 3N aqueous HCl and filtered. The crystalline product was dissolved in 5% methanol in dichloromethane and passed through a short plug of silica gel and activated charcoal. The filtrate was concentrated and chromatographed over silica using 0.5% methanol in dichloromethane as eluant to yield 3.6 g 40% of 1-(3,5-dichloro-4-methoxybenzyl)-2-mercaptobenzimidazole, mp 217°–218°.

EXAMPLE 2

Preparation of 1-(2,6-dichlorobenzyl)-2-mercaptobenzimidazole

A 2,6-Dichlorobenzaldehyde Methoxime

A solution of 2,6-dichlorobenzaldehyde (10 g, 57 mmole) and methoxamine hydrochloride (5.2 g, 63 mmole) in 60 ml of 1:1 ethanol-pyridine was allowed to stir overnight at room temperature. The mixture was evaporated, poured into water and extracted with dichloromethane. The organic layer was washed twice with 3N hydrochloric acid, once with water, once with 5% aqueous sodium bicarbonate then dried ($Na_2SO_4$) and concentrated to give 9.3 g (80%) of the title compound, mp 46°–47°.

B 2,6-Dichlorobenzylamine

A solution of 10 g (49 mmole) of 2,6-dichlorobenzaldehydemethoxime in freshly distilled THF (60 ml) was cooled to 0° and stirred while 51 ml of 0.98M borane in THF was added dropwise. The resulting mixture was heated at reflux for 2 hours and cooled, 20 ml of water were added, followed by 20 ml of 20% aqueous sodium hydroxide. The mixture was heated at reflux for 2 hours, cooled, and extracted twice with diethyl ether. The organic layer was extracted with 3N hydrochloric acid, the aqueous layer was made basic with 50% aqueous sodium hydroxide, and the product was extracted into diethyl ether. The organic extracts were dried ($Na_2SO_4$) and concentrated to give 7.0 g, (82%) of the title compound as a pale yellow oil.

C

N-(2,6-Dichlorobenzyl)-2-nitroaniline

A mixture of 2,6-dichlorobenzylamine (5.8 g, 33 mmole), 2-chloronitrobenzene (1.65 g, 10.5 mmole) and ammonium acetate (0.76 g) was heated at 125° for 30 hours, cooled, diluted with ethyl acetate, and washed with 3N aqueous hydrochloric acid, and then with brine. The solution was dried ($Na_2SO_4$), concentrated, and the residue was purified by flash chromatography using 5% ethyl acetate in hexane as eluant to given 1.5 g (48%) of the title compound as orange crystals, mp 118°–120°.

Alternatively, N-(2,6-dichlorobenzyl)-2-nitroaniline was prepared from 2-fluoronitrobenzene as follows:

A mixture of 2-fluoronitrobenzene (1.9 g, 13.5 mmole) 2,6-dichlorobenzylamine, (7 g, 40 mmole), and ammonium acetate (1 g) was heated at 80° for 1 hour. The cooled mixture was taken up in ethyl acetate and washed sequentially with aqueous 3N hydrochloric acid, water, aqueous 5% sodium bicarbonate, brine, dried ($Na_2SO_4$), and concentrated to give 4.0 g, (96%) of N-(2,6-chlorobenzyl)-2-nitroaniline as orange crystals, mp 118°–120°.

D

N-(2,6-dichlorobenzyl)-2-aminoaniline, and 1-(2,6-dichlorobenzyl)-2-mercaptobenzimidazole Chemical reduction of N-(2,6-dichlorobenzyl)-2-nitroaniline (4.5 g, 9.5 mmole) using the procedure of 1(D) afforded N-(2,6-dichlorobenzyl)-2-aminoaniline. Cyclization with carbon disulfide using the procedure of example 1(D) gave 680 mg, (15%) of 1-(2,6-dichlorobenzyl)-2-mercaptobenzimidazole, mp 234°–235°.

EXAMPLE 3

Preparation of 1-(3,5-difluoro-4-methoxybenzyl)-2-mercaptobenzimidazole

A 3,5-Difluoro-4-methoxybenzaldehyde methoxime 3,5-Difluoro-4-methoxybenzaldehyde (6.5 g, 37.8 mmole) and 3.4 g (41.6 mmole) methoxamine hydrochloride were reacted substantially as described in 1A above to yield 7.4 g (97%) of the title compound as a yellow oil.

B 3,5-Difluoro-4-methoxybenzylamine

The reaction of 3,5-difluoro-4-methoxybenzaldehyde methoxime, (7 g, 35 mmole) and 0.98M borane in tetrahydrofuran (46 ml) substantially as described in 1B above produced 3 g, (50%) of the title compound as a clear oil.

C 3,5-Difluoro-4-methoxybenzyl-2-nitroaniline

A mixture of 2-fluoronitrobenzene (0.82 g, 5.8 mmole), 3,5-difluoro-4-methoxybenzylamine, (3.0 g, 17.3 mmole) and ammonium acetate (0.5 g) was reacted substantially as described in 1C above to yield 1.7 g, (100%) of the title compound as orange crystals.

D

N-(3,5-dichloro-4-methoxybenzyl)-2-aminoaniline, and 1-(3,5-difluoro-4-methoxybenzyl)-2-mercaptobenzimidazole Chemical reduction of the product of C above (2.7 g, 9.2 mmole) using the procedure of examples 1D, followed by cyclization with carbon disulfide as described in 1D above, gave 0.9 g (32%) of 1-(3,5-difluoro-4-methoxybenzyl)-2-mercaptobenzimidazole as a yellow solid.

EXAMPLE 4

Preparation of 1-(3,5-dichlorobenzyl)-2-mercaptobenzimidazole

A 3,5-Dichlorobenzaldehyde methoxime 3,5-Dichlorobenzaldehyde (15 g, 85.7 mmole) and 7.9 g (94.3 mmole), of methoxamine hydrochloride were reacted substantially as described in 1A above to yield 18 g (100%) of title compound mp 55°–56°.

B 3,5-Dichlorobenzylamine

The reaction of 3,5-dichlorobenzaldehyde methoxime, (17.4 g, 85.7 mmole) and 0.98M borane in tetrahydrofuran (86 ml) substantially as described in 1B above produced 10.5 g (70%) of the title compound as a light yellow oil.

C

N-(3,5-Dichlorobenzyl)-2-nitroaniline

A mixture of 2-fluoronitrobenzene (1.2 g, 8.5 mmole) 3,5-dichlorobenzylamine (4.47 g, 25.4 mmole), and ammonium acetate (0.5 g) was reacted substantially as described in 1C above to give 2.5 g (100%) of the title compound as orange crystals: mp 138°–140°.

D

N-(3,5-Dichlorobenzyl)-2-aminoaniline and 1-(3,5-dichlorobenzyl)-2-mercaptobenzimidazole Chemical reduction of the product of (C) above (3.3 g, 11.1 mmole) using the procedure of 1D followed by cyclization with carbon disulfide as described in 1D above gave 0.36 g (10%) of 1-(3,5-dichlorobenzyl)-2-mercaptobenzimidazole as a buff solid, mp 233°.

EXAMPLE 5

Preparation of N-benzyl-2-mercaptobenzimidazole

A

N-Benzyl-2-nitroaniline

Reaction of 2-chloronitrobenzene (10 g, 63 mmole), benzylamine (40 g, 380 mmole) and ammonium acetate (4.6 g) substantially as described in 1C above produced 14 g (98%) of title compound as orange crystals: mp 65°–67°.

B

N-(Benzyl)-2-aminoaniline and N-benzyl-2-mercaptobenzimidazole

Platinum oxide (0.38 g) was prereduced under 50 psi of hydrogen gas in ethanol (50 ml). N-Benzyl-2-nitroaniline, (1.0 g, 4.4 mmole) was added, and the solution was hydrogenated at 50 psi of hydrogen for 3 hours to produce a mixture containing N-benzyl-2-aminoaniline.

The mixture was filtered, and the unpurified filtrate was mixed with carbon disulfide (1.4 g) and a solution of potassium hydroxide (0.38 g) in water (10 ml) and then heated at reflux for 2 hours. The solution was cooled to ambient temperature, diluted with water and acidified with 3N HCl. The crystalline product was collected by filtration and recrystallized from ethanol to give 0.65 g, (62%) of title compound as crystalline needles: mp 184°–185°.

EXAMPLE 6

Preparation of 1-(3,5-difluorobenzyl)-2-mercaptobenzimidazole

A 3,5-Difluorobenzylamine

A solution of 3,5-difluorobenzonitrile (4 g, 28.8 mmole) in methanol saturated with ammonia (100 ml) was added to a slurry of methanol washed Raney nickel. The mixture was shaken under 50 psi hydrogen for 1.5 hours, filtered and the filtrate evaporated. The residue was dissolved in ethyl acetate and extracted with 3N HCl. The acidic solution was basified with 50% sodium hydroxide and was extracted into ethyl acetate. The organic extract was dried ($Na_2SO_4$) and concentrated to give 3.0 g (74%) of title compound as a yellow oil which was stored under nitrogen.

B

N-(3,5-Difluorobenzyl)-2-nitroaniline

Reaction of 2-fluoronitrobenzene (3 g, 21 mmole), 3,5-difluorobenzylamine, (3 g, 21 mmole) and triethylamine (2.6 g, 26.2 mmole) substantially as described in 1C above produced 5.6 g (100%) of title compound as orange crystals: mp 104°–105°.

C

N-(3,5-Difluorobenzyl)-2-aminoaniline and 1-(3,5-Difluorobenzyl)-2-mercaptobenzimidazole Hydrogenation of the nitroaniline, (5.5 g, 20.8 mmole) substantially as described in 5(B) above yielded the intermediate aminoaniline (6 g). Cyclization with carbon disulfide substantially as above yielded 1-(3,5-difluorobenzyl)-2-mercaptobenzimidazole (2.4 g, 42%) as crystalline needles: mp 179°–180°.

EXAMPLE 7

Preparation of 1-(4-methoxybenzyl)-2-mercaptobenzimidazole

A

N-(4-methoxybenzyl)-2-nitroaniline

Reaction of 2-chloronitrobenzene (10 g, 63 mmole), 4-methoxybenzylamine (52.1 g, 380 mmole) and ammonium acetate (4.6 g) substantially as described in 1C above produced 15 g (100%) of title compound as orange crystals: mp 75°–78°.

B

N-(4-methoxybenzyl)-2-aminoaniline and 1-(4-methoxybenzyl)-2-mercaptobenzimidazole Hydrogenation of the nitroaniline, (3.0 g, 11.6 mmole) substantially as described in 5B above yielded the intermediate 2-aminoaniline. Cyclization with carbon disulfide substantially as described in 5B above gave 1.4 g (45%) of 1-(4-methoxybenzyl)-2-mercaptobenzimidazole as crystalline needles, mp 199°–200°.

EXAMPLE 8

Preparation of 1-(3,5-dichloro-4-hydroxybenzyl)-2-mercaptobenzimidazole

A mixture of 1-(3,5-dichloro-4-hydroxybenzyl)-2-mercapto benzimidazole (3.6 g, 10.6 mmoles) in dichloromethane (24 mmole) was stirred at 0° under nitrogen while a solution (1M) of boron tribromide in dichloromethane (32 ml) was added dropwise. After stirring at room temperature for 24 hours, methanol was added dropwise, the mixture was evaporated, the residue taken up in ethyl acetate and the ethyl acetate solution washed with water, brine, dried ($Na_2SO_4$), and concentrated. The solid product was recrystallized from ethyl acetate/hexane to give 1-(3,5-dichloro-4-hydroxybenzyl)-2-mercaptobenzimidazole 2.2 g (64%), mp 246°.

EXAMPLE 9

Preparation of 1-(3,5-difluoro-4-hydroxybenzyl)-2-mercaptobenzimidazole

Reaction of 0.9 g (2.9 mmole) of the product of Example 3 above, using the procedure of Example 8, gave 0.4 g of the title compound mp 200°.

EXAMPLE 10

Preparation of 1-(4-hydroxybenzyl)-2-mercaptobenzimidazole

Reaction of 1.1 g (4.1 mmole) of the product of Example 7 above, using the procedure of Example 8 gave 0.18 g (17%) of the title compound, mp 216°–220°.

EXAMPLE 11

A

1-[3,5-Difluorobenzyl]-2-methylthiobenzimidazole hydroiodide

This compound is prepared by alkylating imidazole (1 g) with methyl iodide according to known literature procedures in a nonreactive solvent, such as methanol, ether or acetone.

The hydrobromide is prepared substantially as above, by substituting methyl bromide for methyl iodide.

The hydrochloride is prepared substantially as above, by substituting methyl chloride for methyl iodide.

B

1-[3,5-Difluorobenzyl]-2-butylthiobenzimidazole hydroiodide

The hydroiodide of the S-butyl compound is prepared substantially as above by substituting butyl iodide as alkylating agent.

Other 1-substituted 2-aralkylthiobenzimidazoles (such as 3,5-dichlorobenzyl, 3,5-difluorophenylpropyl, 3,5-dichlorophenylpropyl, etc.) are prepared from the appropriate 2-mercaptobenzimidazole and an appropriate lower alkyl ($C_{1-4}$) halide (chloride, bromide, iodide). Alternatively, any salt above may be neutralized to the free base with, for example, sodium hydroxide, or sodium carbonate, and then converted to another pharmacologically acceptable addition salt by adding the appropriate acid to a solution of the free base in a nonreactive solvent such as methanol, ether, acetone, etc.

EXAMPLES 12-36

The compounds shown in Table III, which follows are prepared substantially by procedures illustrated in the preceding examples except that suitable molar amounts of appropriate starting materials and reagents are used.

TABLE III

| Example No. | Y | $n^2$ | $R^3$ | $R^4$ | $R^5$ | $R^6$ | R |
|---|---|---|---|---|---|---|---|
| 12 | SH | 0 | H | F | H | H | H |
| 13 | SH | 1 | H | F | H | H | H |
| 14 | SH | 2 | H | F | H | H | H |
| 15 | SH | 3 | H | F | H | H | H |
| 16 | SH | 4 | H | F | H | H | H |
| 17 | SH | 0 | H | F | H | F | H |
| 18 | SH | 2 | H | F | H | F | H |
| 19 | SH | 3 | H | F | H | F | H |
| 20 | SH | 4 | H | F | H | F | H |
| 21 | SH | 3 | H | F | OH | F | H |
| 22 | $SCH_3$ | 3 | H | F | OH | F | H |
| 23 | SH | 4 | H | F | OH | F | H |
| 24 | SH | 3 | H | Cl | H | Cl | H |
| 25 | SH | 3 | H | Cl | OH | Cl | H |
| 26 | SH | 1 | H | $CF_3$ | OH | H | H |
| 27 | SH | 1 | H | $CF_3$ | $OH_3$ | CF | H |
| 28 | SH | 3 | H | $SO_2CF_3$ | OH | H | H |
| 29 | $S(CH_2)_3CH_3$ | 1 | H | H | OH | H | H |
| 30 | SH | 1 | H | F | OH | Cl | H |
| 31 | SH | 1 | H | $CONH_2$ | OH | H | H |
| 32 | SH | 1 | H | CN | OH | H | H |
| 33 | $SCH_2CH_3$ | 3 | H | CN | OH | H | H |
| 34 | SH | 1 | H | F | OH | H | H |
| 35 | SH | 1 | H | Cl | OH | H | H |
| 36 | SH | 1 | H | Br | OH | H | H |

EXAMPLE 37

1-Benzyl-2-aminomethylbenzimidazole hydrochloride

A

1-Benzyl-2-chloromethylbenzimidazole hydrochloride

A solution of N-benzyl-2-nitroaniline (22.3 g, 0.1 mole) in ethyl acetate (100 ml) was hydrogenated for 25 hours at 50 psi of hydrogen over Raney nickel (3 ml). The solution was filtered, concentrated and the resulting green residue was heated at reflux for 4 hours with concentrated hydrochloric acid (38 ml), water (12 ml) and chloroacetic acid (18.9 g, 0.2 mole). The mixture was cooled, neutralized with 50% aqueous NaOH to pH 6, and extracted three times with diethyl ether. The organic extracts were washed with water, brine, dried ($Na_2SO_4$), and saturated with hydrogen chloride gas to yield 24.25 g (83%) of product as tan crystals: mp 94°-98° (dec).

B

1-Benzyl-2-azidomethylbenzimidazole

A solution of 1-Benzyl-2-chloromethylbenzimidazole hydrochloride (16 g, 0.055 mole) in N,N-dimethylformamide (80 ml) was stirred and a solution of sodium azide (17 g, 0.26 mole) in water (40 ml) was added. The resulting yellow solution was heated on a steam bath for 30 minutes, diluted with water (250 ml) and the crystalline product was filtered, dried in vacuo at room temperature, and recrystallized from 2-propanol to yield 10.5 g (73%) of product: mp 108°-110°.

C

1-Benzyl-2-aminomethylbenzimidazole hydrochloride

A solution of 1-benzyl-2-azidomethyl-benzimidazole (3 g, 0.0114 mole) in ethyl acetate (100 ml) was hydrogenated at 50 psi hydrogen pressure over 10% palladium on charcoal for 1 hour. The mixture was filtered, concentrated under reduced pressure, and the residue was chromatographed on silica gel using 1:1 methanol-ethyl acetate as eluant. The chromatographed product was dissolved in hot absolute ethanol (5 ml) and treated with a 2N solution of hydrogen chloride in ethanol to yield the hydrochloride salt (1.37 g, 43%) as white crystals: mp 260°-262° (dec).

EXAMPLE 38

1-[3,4-Dichlorobenzyl]-2-aminomethylbenzimidazole dihydrochloride

A

1-[3,4-Dichlorobenzyl]-2-chloromethylbenzimidazole

The hydrogenation of N-[3,4-dichlorobenzyl]-2-nitroaniline (29 g, 0.1 mole) and subsequent condensation of the intermediate aminoaniline proceeded substantially as above except the diethyl ether extracts were dried and diluted with hexane to yield 10.75 g (37%) of product as the free base: mp 127°-129° (dec).

B

1-[3,4-Dichlorobenzyl]-2-azidomethylbenzimidazole

The reaction of 1-[3,4-dichlorobenzyl]-2-chloromethylbenzimidazole (10 g, 0.0307 mole) substantially as above yielded 5 g (49%) of product: mp 78°-80°.

C

1-[3,4-Dichlorobenzyl]-2-aminomethylbenzimidazole dihydrochloride

A solution of 1-[3,4-dichlorobenzyl]-2-azidomethyl-benzimidazole (1 g, 0.003 mole) in ethanol (40 ml) was hydrogenated over Raney nickel (3 ml) at 50 psi of hydrogen for 1.5 hours, filtered and concentrated. The residue was chromatographed on silica gel using 2:1 ethyl acetate-hexane as eluant. The chromatographed product was dissolved in absolute ethanol (20 ml) and treated with a solution of hydrogen chloride in ether to yield 875 mg (77%) of the dihydrochloride salt: mp 183°-186° (dec).

EXAMPLE 39

Preparation of 1-[3-fluorobenzyl]-2-aminomethylbenzimidazole dihydrofluoride

A

1-[3-fluorobenzyl]-2-chloromethylbenzimidazole

Hydrogenation of N-[3-fluorobenzyl]-2-nitroaniline substantially as described in 37A above gave the title compound as the free base.

B

1-[3-fluorobenzyl]-2-azidomethylbenzimidazole

Reaction of 1-3-fluorobenzyl-2-chloromethylbenzimidazole as described in 37B above gave the title compound as the free base.

C

1-[3-fluorobenzyl]-2-aminomethylbenzimidazole dihydrofluoride

Reaction of the product of B above as described in 37C above using hydrogen fluoride in place of hydrogen chloride gave 1-[3-fluorobenzyl]-2-aminomethylbenzimidazole dihydrofluoride, mp 190°–193°.

EXAMPLE 40

Preparation of 1-[3-chlorobenzyl]-2-aminomethylbenzimidazole dihydrochloride

A

1-[3-chlorobenzyl]-2-chloromethylbenzimidazole

Hydrogenation of N-[3-chlorobenzyl]-2-nitroaniline substantially as described in 37A above gave the title compound as the free base.

B

1-[3-chlorobenzyl]-2-azidomethylbenzimidazole

Reaction of 1-[3-chlorobenzyl]-2-chloromethylbenzimidazole as described in 37B above gave the title compound as the free base.

C

1-[3-chlorobenzyl]-2-aminomethylbenzimidazole dihydrochloride

Reaction of the product of B above as described in 37C above gave 1-[3-chlorobenzyl]-2-aminomethylbenzimidazole dihydrochloride mp 169°–172°.

EXAMPLES 41 TO 62

The compounds shown in Table IV which follows, are prepared substantially by the procedures illustrated in the preceding examples No. 37 and 38, except that suitable molar amounts of appropriate starting materials and other reagents are used.

TABLE IV

| Example No. | Y | $n^2$ | $R^3$ | $R^4$ | $R^5$ | $R^6$ | R |
|---|---|---|---|---|---|---|---|
| 41 | $CH_2NH_2$ | 2 | Cl | Cl | H | H | H |
| 42 | $CH_2NH_2$ | 1 | H | F | H | F | H |
| 43 | $CH_2NH_2$ | 1 | H | Cl | H | Cl | H |
| 44 | $CH_2NH_2$ | 1 | H | F | OH | F | H |
| 45 | $CH_2NH_2$ | 1 | H | Cl | OH | Cl | H |
| 46 | $CH_2NH_2$ | 3 | H | F | H | F | H |
| 47 | $CH_2NH_2$ | 3 | H | Cl | H | Cl | H |
| 48 | $CH_2NH_2$ | 3 | H | F | OH | F | H |
| 49 | $CH_2NH_2$ | 3 | H | Cl | OH | Cl | H |
| 50 | $CH_2NH_2$ | 2 | H | F | OH | F | H |
| 51 | $CH_2NH_2$ | 1 | H | Cl | OH | H | H |
| 52 | $CH_2NH_2$ | 1 | H | F | OH | H | H |
| 53 | $CH_2NH_2$ | 3 | H | Cl | OH | H | H |
| 54 | $CH_2NH_2$ | 3 | H | F | OH | H | H |
| 55 | $CH_2NH_2$ | 4 | H | F | H | F | H |
| 56 | $CH_2NH_2$ | 3 | H | F | OH | Cl | H |
| 57 | $CH_2NH_2$ | 1 | H | $CF_3$ | OH | H | H |
| 58 | $CH_2NH_2$ | 2 | H | $NO_2$ | OH | H | H |
| 59 | $CH_2NH_2$ | 3 | H | $CF_3$ | $OCH_3$ | H | H |
| 60 | $CH_2NH_2$ | 4 | H | $SO_2NH_2$ | OH | H | H |
| 61 | $CH_2NH_2$ | 1 | H | Br | H | Br | H |
| 62 | $CH_2NH_2$ | 1 | H | I | H | I | H |

EXAMPLE 63

The ingredients in Table V below are screened, mixed and filled into a hard gelatin capsule.

TABLE V

| Ingredients | Amounts |
|---|---|
| 1-(3,5-Dichloro-4-methoxybenzyl)-2-mercaptobenzimidazole | 50 mg |
| magnesium stearate | 5 mg |
| lactose | 75 mg |

EXAMPLE 64

The sucrose, calcium sulfate dihydrate and imidazole shown in Table VI below, are mixed and granulated with a 10% gelatin solution. The wet granules are screened, dried, mixed with the starch, talc and stearic acid, screened and compressed into a tablet.

TABLE VI

| | |
|---|---|
| 1-(3,5-Difluoro-4-methoxybenzyl)-2-mercaptobenzimidazole | 100 mg |
| calcium sulfate dihydrate | 150 mg |
| sucrose | 20 mg |
| starch | 10 mg |
| talc | 5 mg |
| stearic acid | 3 mg |

EXAMPLE 65

1-(3,5-Dichlorobenzyl)-2-mercaptobenzimidazole, 75 mg, is suspended in 25 ml of normal saline to prepare an injectable preparation.

While the preferred embodiments of the invention are illustrated by the above, it is to be understood that the invention is not limited to the precise constructions herein disclosed and that the right to all modifications coming within the scope of the following claims is reserved.

What we claim is:

1. A pharmaceutical composition having dopamine-β-hydroxylase inhibiting activity comprising an effective amount of a compound of structure (II)

(II)

in which:
Y is $CH_2NH_2$ or SR;
R is hydrogen or $C_{1-4}$ alkyl;
n is 0 to 5; and
$R^2$ to $R^6$ are the same or different and are each hydrogen, halogen, hydroxy, $C_{1-4}$ alkyl, CN, $NO_2$, $SO_2NH_2$, $CO_2H$, $CONH_2$, CHO, $CH_2OH$, $CF_3$, $C_{1-4}$alkoxy, $SO_2C_{1-4}$alkoxy, $SO_2C_{1-4}$fluoroalkyl or $CO_2C_{1-4}$alkyl, provided that, when Y is SH, $R^2$, $R^3$, $R^5$ and $R^6$ are all hydrogen and n is 0, $R^4$ is not methoxy;

or a pharmaceutically acceptable salt or hydrate thereof in association with a pharmaceutically acceptable carrier.

2. A pharmaceutical composition as claimed in claim 1 in which Y is SR and R is hydrogen.

3. A pharmaceutical composition as claimed in claim 2 in which n is 1, $R^3$ and $R^5$ are halogen and $R^2$, $R^4$ and $R^6$ are all hydrogen.

4. A pharmaceutical composition as claimed in claim 2 in which n is 1, $R^3$ and $R^5$ are halogen, $R^2$ and $R^6$ are hydrogen and $R^4$ is hydroxy.

5. A pharmaceutical composition as claimed in claim 2 in which $R^3$ and $R^5$ are the same and are fluorine or chlorine.

6. A pharmaceutical composition as claimed in claim 2 in which the compound of structure (II) is:
1-(3,5-dichloro-4-methoxybenzyl)-2-mercaptobenzimidazole.

7. A pharmaceutical composition as claimed in claim 2 in which the compound of structure (II) is:
1-(2,6-dichlorobenzyl)-2-mercaptobenzimidazole.

8. A pharmaceutical composition as claimed in claim 2 in which the compound of structure (II) is:
1-(3,5-difluoro-4-methoxybenzyl)-2-mercaptobenzimidazole.

9. A pharmaceutical composition as claimed in claim 2 in which the compound of structure (II) is:
1-(3,5-dichlorobenzyl)-2-mercaptobenzimidazole.

10. A pharmaceutical composition as claimed in claim 2 in which the compound of structure (II) is:
N-benzyl-2-mercaptobenzimidazole.

11. A pharmaceutical composition as claimed in claim 2 in which the compound of structure (II) is:
1-(3,5-difluorobenzyl)-2-mercaptobenzimidazole.

12. A pharmaceutical composition as claimed in claim 2 in which the compound of structure (II) is:
1-(4-methoxybenzyl)-2-mercapto-benzamidazole.

13. A pharmaceutical composition as claimed in claim 2 in which the compound of structure (II) is:
1-(3,5-dichloro-4-hydroxybenzyl)-2-mercaptobenzimidazole.

14. A pharmaceutical composition as claimed in claim 2 in which the compound of structure (II) is:
1-(3,5-difluoro-4-hydroxybenzyl)-2-mercaptobenzimidazole.

15. A pharmaceutical composition as claimed in claim 2 in which the compound of structure (II) is:
1-(4-hydroxybenzyl)-2-mercaptobenzimidazole.

16. A pharmaceutical composition as claimed in claim 2 in which Y is —$CH_2NH_2$.

17. A pharmaceutical composition as claimed in claim 16 in which n is 1 and $R^2$ to $R^6$ are all hydrogen.

18. A pharmaceutical composition as claimed in claim 16 in which n is 1, $R^4$ and $R^5$ are halogen and $R^2$, $R^3$ and $R^6$ are all hydrogen.

19. A pharmaceutical composition as claimed in claim 16 in which the compound of structure (II) is:
1-benzyl-2-aminomethylbenzimidazole hydrochloride.

20. A pharmaceutical composition as claimed in claim 16 in which the compound of structure (II) is:
1-[3,4-dichlorobenzyl]-2-aminomethylbenzimidazole dihydrochloride.

21. A pharmaceutical composition as claimed in claim 16 in which the compound of structure (II) is:
1-[3-fluorobenzyl]-2-aminomethylbenzimidazoledihydrochloride.

22. A pharmaceutical composition as claimed in claim 16 in which the compound of structure (II) is:
1-[3-chlorobenzyl]-2-aminomethylbenzimidazole dihydrofluoride.

23. A method of inhibiting dopamine-β-hydroxylase activity in mammals which comprises administering internally to a subject in need thereof an effective amount of a compound of structure (III),

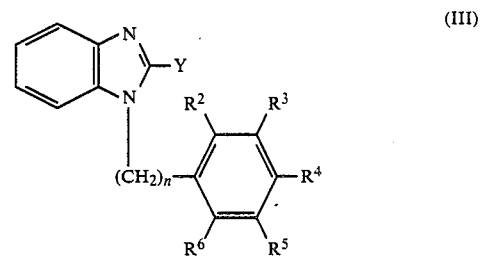

(III)

in which,
Y is a group —$CH_2NH_2$ or SR;
R is hydrogen or $C_{1-4}$alkyl;
n is 0 to 5; and
$R^2$ to $R^6$ are the same or different and are each hydrogen, halogen, hydroxy, $C_{1-4}$ alkyl, CN, $NO_2$, $SO_2NH_2$, $CO_2H$, $CONH_2$, CHO, $CH_2OH$, $CF_3$, $C_{1-4}$alkoxy, $SO_2C_{1-4}$alkoxy, $SO_2C_{1-4}$-fluoroalkyl or $CO_2C_{1-4}$alkyl;

or a pharmaceutically acceptable salt or hydrate thereof.

24. The method of claim 23 in which Y is SR and R is hydrogen.

25. The method of claim 24 in which n is 1, $R^3$ and $R^5$ are halogen and $R^2$, $R^4$ and $R^6$ are each hydrogen.

26. The method of claim 24 in which n is 1, $R^3$ and $R^5$ are halogen, $R^2$ and $R^6$ are hydrogen and $R^4$ is hydroxy.

27. The method of claim 23 or 24 in which $R^3$ and $R^5$ are the same and are each selected from chlorine and fluorine.

28. The method of claim 23 in which the compound structure (III) is:
1-(3,5-dichloro-4-methoxybenzyl)-2-mercaptobenzimidazole.

29. The method of claim 23 in which the compound structure (III) is:
1-(2,6-dichlorobenzyl)-2-mercaptobenzimidazole.

30. The method of claim 23 in which the compound structure (III) is:
1-(3,5-difluoro-4-methoxybenzyl)-2-mercaptobenzimidazole.

31. The method of claim 23 in which the compound structure (III) is:
1-(3,5-dichlorobenzyl)-2-mercaptobenzimidazole.

32. The method of claim 23 in which the compound structure (III) is:
N-benzyl-2-mercaptobenzimidazole.

33. The method of claim 23 in which the compound structure (III) is:
1-(3,5-difluorobenzyl)-2-mercaptobenzimidazole.

34. The method of claim 23 in which the compound structure (III) is:
1-(4-methoxybenzyl)-2-mercaptobenzimidazole.

35. The method of claim 23 in which the compound structure (III) is:

1-(3,5-dichloro-4-hydroxybenzyl)-2-mercaptobenzimidazole.

36. The method of claim 23 in which the compound structure (III) is:
1-(3,5-difluoro-4-hydroxybenzyl)-2-mercaptobenzimidazole.

37. The method of claim 23 in which the compound structure (III) is:
1-(4-hydroxybenzyl)-2-mercaptobenzimidazole.

38. The method of claim 23 in which Y is $CH_2NH_2$.

39. The method of claim 38 in which n is 1 and $R^2$ to $R^6$ are all hydrogen.

40. The method of claim 38 in which n is 1, $R^4$ and $R^5$ are halogen and $R^2$, $R^3$ and $R^6$ are all hydrogen.

41. The method of claim 38 in which the compound of structure (III) is:
1-benzyl-2-aminomethylbenzimidazole hydrochloride.

42. The method of claim 38 in which the compound of structure (III) is:
1-[3,4-dichlorobenzyl]-2-aminomethylbenzimidazole dihydrochloride.

43. The method of claim 38 in which the compound of structure (III) is:
1-[3-fluorobenzyl]-2-aminomethylbenzimidazole-dihydrochloride.

44. The method of claim 38 in which the compound of structure (III) is:
1-[3-chlorobenzyl]-2-aminomethylbenzimidazole-dihydrofluoride.

* * * * *